United States Patent
Zhang et al.

(10) Patent No.: US 10,145,799 B2
(45) Date of Patent: Dec. 4, 2018

(54) FIBER-COUPLED METAL-TIP NEAR-FIELD CHEMICAL IMAGING SPECTROSCOPY

(71) Applicant: BAYLOR UNIVERSITY, Waco, TX (US)

(72) Inventors: Zhenrong Zhang, Waco, TX (US); Blake Birmingham, Waco, TX (US); Ho Wai Howard Lee, Waco, TX (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 15/902,605

(22) Filed: Feb. 22, 2018

(65) Prior Publication Data

US 2018/0238806 A1    Aug. 23, 2018

Related U.S. Application Data

(60) Provisional application No. 62/462,225, filed on Feb. 22, 2017.

(51) Int. Cl.

| | |
|---|---|
| *G01N 21/00* | (2006.01) |
| *G01N 21/65* | (2006.01) |
| *G01N 21/552* | (2014.01) |
| *G01J 3/44* | (2006.01) |
| *G01Q 30/02* | (2010.01) |
| *G01Q 60/22* | (2010.01) |

(52) U.S. Cl.
CPC .......... *G01N 21/658* (2013.01); *G01J 3/4412* (2013.01); *G01N 21/554* (2013.01); *G01Q 30/025* (2013.01); *G01Q 60/22* (2013.01)

(58) Field of Classification Search
CPC ... G01J 3/02; G01J 3/44; G01N 21/65; G01N 21/55; G01Q 30/025; G01Q 60/22
See application file for complete search history.

(56) References Cited

U.S. PATENT DOCUMENTS

| | | | |
|---|---|---|---|
| 8,984,661 | B2 | 3/2015 | Weber-Bargioni et al. |
| 2016/0049215 | A1* | 2/2016 | Dionne .................. G21K 1/006 250/251 |

OTHER PUBLICATIONS

Niedermeyr, G., International Search Report for International Patent Application No. PCT/US2018/019202, dated Jun. 6, 2018, European Patent Office.

Flentje, F., Written Opinion for International Patent Application No. PCT/US2018/019202, dated Jun. 6, 2018, European Patent Office.

Watanabe, K., et al., "Conductive optical-fiber STM probe for local excitation and collection of cathodoluminescene at semiconductor surfaces", Optics Express, Aug. 6, 2013, pp. 19261-19268, vol. 21, No. 16.

(Continued)

*Primary Examiner* — Abdullahi Nur

(74) *Attorney, Agent, or Firm* — Jackson Walker, LLP

(57) ABSTRACT

The present disclosure provides a system and method for a fiber-coupled, metal-tip chemical imaging spectroscopy. The system couples the electromagnetic radiation (EMR), such as laser light, through an optical fiber to a conductive tip for both EMR excitation to the sample through the conductive tip and EMR signal collection from the sample through the conductive tip. The system and method effectively eliminates the need for an optical alignment between the EMR source and the tip, and still offers the customary spatial resolution of a non-coupled system.

20 Claims, 11 Drawing Sheets

(56) References Cited

OTHER PUBLICATIONS

Alessandro, T and Scmidt, M., "Broadband efficient directional coupling to short-range plasmons: towards hybrid fiber nanotips", Optics Express, Apr. 4, 2016, pp. 7507-7524, vol. 24, No. 7.

Schmidt, M., "Gold nanowires enable plasmonics in optical fibers", SPIE Newsroom, Jul. 14, 2014, 3 pages, 10.1117/2.1201406.005493.

Alessandro, T. et al., "Hybrid-Mode-Assisted Long-Distance Excitation of Short-Range Surface Plasmons in a Nanotip-Enhanced Step-Index Fiber", Nano Letters, Dec. 16, 2016, pp. 631-637, vol. 17, No. 2.

Pesapane, A., et al., "Fiber-optic SERS sensor with optimized geometry: testing and optimization", Journal of Raman Spectroscopy, Sep. 18, 2009, pp. 256-267, vol. 41, Issue 3.

Boa, W., et al., "Mapping Local Charge Recombination Heterogeneity by Multidimensional Nanospectroscopic Imaging", Science, Dec. 7, 2012, pp. 1317-1321, vol. 338, No. 6112.

Boa, W., et al., "Supplementary Materials for Mapping Local Charge Recombination Heterogeneity by Multidimensional Nanospectroscopic Imaging", Science AAAS, Dec. 7, 2018, 14 pages.

\* cited by examiner

FIBER-COUPLED METAL-TIP NEAR-FIELD CHEMICAL IMAGING SPECTROSCOPY

CROSS REFERENCE TO RELATED APPLICATIONS

This application claims the benefit of U.S. Provisional Ser. No. 62/462,225, filed on Feb. 22, 2017 and is incorporated herein by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates to system and method for spectroscopy. More specifically, the disclosure relates to a system and method for enhanced transmission of light in spectroscopy for analysis of materials.

Description of the Related Art

Spectroscopy is the study of the interaction between matter and electromagnetic radiation ("EMR"), such as light. Spectroscopic data is often represented by an emission spectrum, which is a plot of the response of a material as a function of wavelength or frequency of the EMR. Different materials have different responses to different EMR and the response forms a signature that can be used to identify the material. Further, the response can be used to identify features and characteristics of the material, such as shapes, orientations, and other features of the subject. Examples of types of spectroscopy include: absorption spectroscopy for energy absorption by the material, emission spectroscopy for energy release by the material; elastic scattering and reflection spectroscopy for incident radiation reflection or scattering by a material; impedance spectroscopy for material slowing the transmittance of energy; inelastic scattering for an exchange of energy between the radiation and the matter shifts the wavelength of the scattered radiation, including Raman scattering, and others.

Raman spectroscopy is a spectroscopic technique used to observe vibrational, rotational, and other low-frequency modes of a material, and is used in chemistry to provide a fingerprint to identify molecules. The technique relies on inelastic scattering ("or "Raman scattering") of monochromatic light, usually from a laser in the visible, near infrared, or near ultraviolet range. The laser light interacts with molecular vibrations, phonons or other excitations in the material, resulting in the energy of the laser photons being shifted up or down. The shift in energy gives information about the vibrational modes in the material. There are a number of advanced types of Raman spectroscopy, including surface-enhanced Raman, resonance Raman, tip-enhanced Raman, polarized Raman, stimulated Raman (analogous to stimulated emission), transmission Raman, spatially offset Raman, and hyper Raman.

FIG. 1 is a schematic diagram of a typical objective tip-enhanced Raman spectroscope (TERS). A TERS system combines scanning probe microscope (SPM) technology with Raman spectroscopy. TERS offers the highest spatial resolution without molecule labeling. A TERS system has the capability of imaging chemical composition and three-dimensional spatial morphology of sample surfaces from the same nanoscale location. In a typical TERS 2, a laser light beam 8 as a form of EMR is focused through an objective lens 10 to a zone 12 of about 1 micron (μm) to illuminate a sample 4 on a supporting support 6. The reflected light is collected through the objective lens 10 and is transmitted through optical components 20 to an analyzer 18, such as a spectrometer, for processing.

A controller 24 (that can include a scanner) controls a nano-sized guide wire 14 of about 200-500 nanometers (nm) with a tip of about 2-20 nm. The guide wire 14 is used to scan the surface of the sample 4. TERS typically has a spatial resolution of about 10 nm in chemical imaging. Elastic scattered radiation (or "Rayleigh scattering") at the wavelength corresponding to the laser line is filtered out, while the rest of the collected light representing the inelastic Raman scattering is dispersed onto a detector of the analyzer.

While the simple schematic in FIG. 1 is helpful to illustrate concepts, in actuality, the equipment of the TERS 2 is complicated. One of the main drawbacks of current TERS apparatuses is its restricted optical alignment that has hindered the wide practical applications of TERS. Nanoscale optical spectroscopy requires the efficient delivery of light for a spatially nano-confined excitation. The main difficulty comes from the optical alignment of the micro-scale focused laser beam to the nanoscale conductive tip. In order to increase the weak Raman signal level, it is necessary to focus the laser beam close to a diffraction limit (<1 μm). The light beam must be focused down to the sample at a beam of about 1 micron and aligned with the 2-20 nm tip that is 50-500 times smaller. A small misalignment (~100 nm) of laser beam, which has large spatial variation of the E-field results in a dramatic signal decrease. Therefore, alignment makes TERS imaging a time-consuming experiment with low reproducibility. Low excitation efficiency, high far-field background noise, and low collection efficiency are other factors that present challenges for general applications of TERS with these conventional configurations. The direct illumination of the tip apex results in a three-to-four order of magnitude loss in excitation efficiency. This is due to the mode mismatch between the diffraction-limited far-field laser excitation focus and the desired tens of nanometer near-field localization determined by the tip apex radius. In addition, the light beam is larger than the tip, so the light beam reflects from the surface surrounding the tip and creates background noise. The micron-size laser beam excites a micron-size background that creates a far-field background signal that needs filtering to analyze the spatially resolved weak Raman signal from the tip enhancement. This far-field noise significantly limits the imaging contrast. As for collection, only a few percent (~3%) of scattered Raman signals could be collected via optical lens. Still further, general procedures require making numerous tips and then testing the tips to determine suitability for a given light spectrum to function with the tip. Each tip must be aligned as mentioned above to perform the test.

In at least one instance, an optical fiber cable has been coupled with the guide wire 14 to an analyzer to transmit the resulting EMR (in this case, from the laser light beam shown on the sample) from the guide wire to the analyzer. (P. Uebel, et al., A gold-nanotip optical fiber for plasmon-enhanced near-field detection, Appl. Phys. Lett. 103, 021101 (2013).). However, the guide wire was not used to provide the light, in addition to collect the resulting EMR.

Therefore, there remains a need for an improved system and method that can efficiently and quickly align the light beam with the probe, with less complexity, and further to receive a signal with less noise from less surface effect on the resulting signal.

BRIEF SUMMARY OF THE INVENTION

The present disclosure provides a system and method for a fiber-coupled, nano-sized, conductive-tip chemical imaging spectroscopy. The system couples the electromagnetic radiation (EMR), such as laser light, through an optical fiber to a conductive tip for both EMR excitation to the sample through the conductive tip and EMR signal collection from the sample through the conductive tip. The system and method effectively eliminates the need for an optical alignment between the EMR source and the tip, and still offers the customary spatial resolution of a non-coupled system. Three examples of conductive tips are disclosed including a metal tip (such as gold or silver) filled or otherwise inserted in an opening of an optical fiber; a coated tip with one or more conductive layers, such as with a metal, conducting oxides, or metal nitride, and other compound conductors; and a conductive tip in a photonic crystal fiber. The disclosure addresses major factors that have hindered the general applications of TERS such as low excitation efficiency, high far-field background noise, and low collection efficiency.

The disclosure provides a spectroscopy system, comprising: an optical fiber; a plasmonic tip coupled with the optical fiber configured to be energized into a plasmonic mode; a controller operatively coupled to the optical fiber and configured to control an electromagnetic radiation (EMR) source to provide one or more frequencies to the optical fiber as an excitation EMR, the frequency being at a plasmonic resonance with the plasmonic tip to transmit the excitation EMR in various forms through the optical fiber to the tip; and a receiver operatively coupled to the optical fiber and configured to receive a signal EMR in various forms from the tip through the optical fiber, the signal EMR being different from the excitation EMR.

The disclosure also provides a method of analyzing a sample with a spectroscopy system, the spectroscopy, comprising an optical fiber; a tip coupled to the optical fiber; a controller operatively coupled to the optical fiber; and a receiver operatively coupled to the optical fiber, the method comprising: creating an electromagnetic radiation (EMR) at a predetermined plasmonic resonance frequency as an excitation EMR; converting at least a portion of the excitation EMR to a wave guide excitation EMR; guiding the wave guide excitation EMR along the optical fiber toward the tip; converting at least a portion of the excitation EMR to a plasmonic excitation EMR; propagating the plasmonic excitation EMR along the tip; allowing the plasmonic excitation EMR to transmit a focused transfer excitation EMR from the tip across a space to a sample; changing a molecular vibrational status of the sample with the focused transfer excitation EMR; creating a reflected signal EMR from the sample at a different frequency than the transfer excitation EMR from the tip; receiving at least a portion of the reflected signal EMR from the sample across the space to the tip; allowing the reflected EMR from the sample to the tip to create a plasmonic signal EMR; propagating the plasmonic signal EMR along the tip; converting at least a portion of the plasmonic signal EMR to a wave guide signal EMR; guiding the wave guide signal EMR along the optical fiber to the receiver; and analyzing the signal EMR from the optical fiber to determine a characteristic of the sample.

DETAILED DESCRIPTION

Figure 1A:
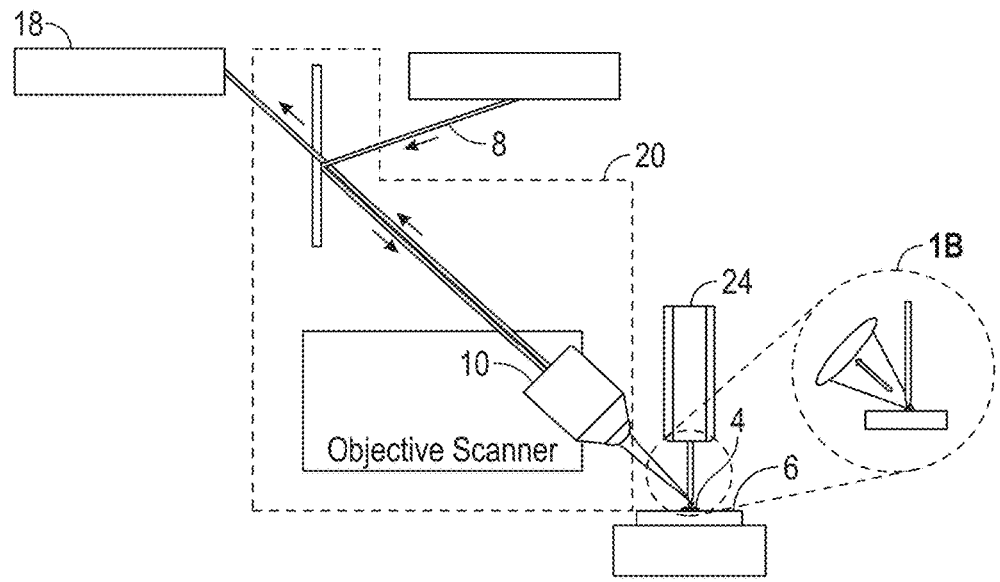
FIG. 1A is a schematic diagram of a typical objective tip-enhanced Raman spectroscope (TERS).
Figure 1B:
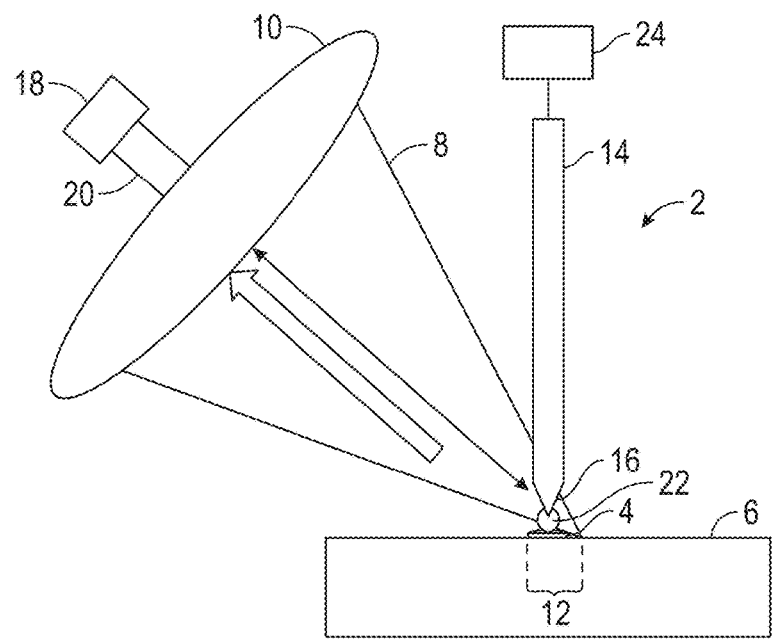
FIG. 1B is a schematic diagram of an enlarged portion of the spectroscope schematic in FIG. 1A.

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation or location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Some elements are nominated by a device name for simplicity and would be understood to include a system or a section, such as a processor would encompass a processing system of related components that are known to those with ordinary skill in the art and may not be specifically described.

The present disclosure provides a system and method for a fiber-coupled, nano-sized, conductive-tip chemical imaging spectroscopy. The disclosure describes a new near-field chemical imaging microscopy based on a fiber-tip assembly having an optical fiber with a conductive nano-tip and/or coated with conducting materials. In this non-optical alignment TERS scheme, the excitation and collection is via the same fiber-tip assembly, which enables the TERS to be a practical and potentially portable chemical imaging spectroscopy for various field applications in material science, bio-medical, optoelectronic, catalysis, etc. The system couples the electromagnetic radiation (EMR), such as laser light, through the optical fiber to the conductive tip for both EMR excitation to the sample through the conductive tip and EMR signal collection from the sample through the conductive tip and back through the optical fiber. The system and method effectively eliminates the need for an optical alignment between the EMR source and the tip, and still offers the customary spatial resolution of a non-coupled system.

It is expected that the invention advantageously offers one or more of the following features:
  Fewer optical components, particularly related to alignment components, because no alignment between the EMR and the tip is needed when the EMR is transmitted through the guidewire tip to the sample, because the EMR is automatically wherever the tip is;
  Coupling the EMR from the optical fiber to the tip and a response EMR from the tip into the same optical fiber.
  More efficiency on the EMR transmission to the sample because the EMR is transmitted through the tip to be focused on the sample and less to a surrounding surface;
  Isolated surface effect with less background noise due to the EMR transmission through the tip to the sample and less to the surrounding surface, causing a better signal to noise ratio;
  Better TERS success rate by providing the capability to pretune a tip plasmonic resonance to match an excitation EMR because a broad band EMR can be transmitted through the tip for multiple frequencies without alignments required from an externally aligned EMRs;
  Portability of a spectroscopic chemical imaging system and ease of operation without need for complex alignment components requiring a large platform with specialized training in set up;
  Ease of integration with existing probe microscope designs due to the optical fiber coupled with the guidewire; and
  Space saving footprint using an optical fiber and guidewire assembly of about 0.5 mm or less without large and complex alignment components.

The system utilizes a conducting material (gold, conducting oxide, or metal nitride) filled and/or coated optical fiber as the nano-tip and the integrated optical fiber for excitation and collection. The EMR, such as laser light, highly confined in the core of a fiber, directly couples to the propagating surface plasmon mode of the conducting material, and is then adiabatically focuses to the tip apex to form a "hot spot" for Raman enhancement. A plasmon is known to be a quantum of plasma oscillation. As light consists of photons, the plasma oscillation consists of plasmons. The plasmon can be considered as a quasiparticle since it arises from the quantization of plasma oscillations, as phonons are quantizations of mechanical vibrations. A plasmon mode is a mode of energy in a material that can conduct plasmons along the material. Similarly, a plasmonic material is a material that is allows plasmons be conducted along the material. The Raman signal is collected via the reverse coupling process. The system and method eliminates the need for optical alignment of the laser to the plasmonic tip, which significantly simplifies the operation while still offering the spatial and chemical resolution of TERS. The direct coupling of highly confined light guided in fibers to the propagating plasmonic mode offers high levels of excitation and collection efficiency. Fabricating the fiber and the nano-tip together allows practical adoption of this TERS system in various complex realistic environments with high spatial resolution, such as controlled gaseous, liquid, and electrolyte environments.

Some embodiments integrate the nanofilms of metal, insulator, and transparent conducting oxide (TCO) onto the fiber probe formed with a fiber tip for electrically tunable plasmonic coupling in gaseous, liquid, and electrolyte environments. In comparison to traditional noble metal designs, conducting oxide plasmonics material coated on optical fibers can further improve the Raman signal intensity by reducing loss of the propagating surface plasmon. TCOs and other similar materials are alternatives to plasmonic materials, because they exhibit metallic properties in the visible and near-infrared spectral range with lower material loss than noble metals. Further, their complex dielectric function can be modulated under an applied voltage bias through field effect dynamics in a metal-oxide-semiconductor (MOS) structure. This modulation enables the possibility of a tunable TERS system.

Figure 2A:
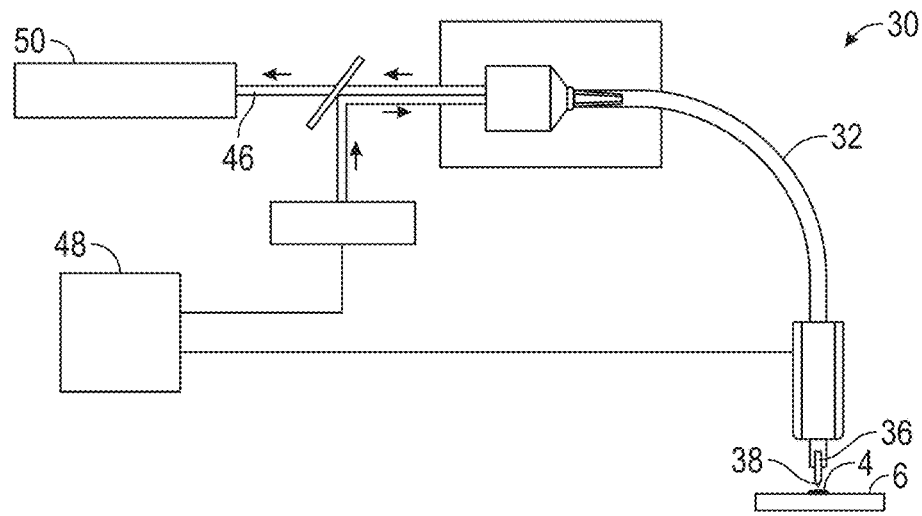
FIG. 2A is a schematic diagram of an illustrative embodiment of an improved TERS system according to the invention.
Figure 2B:
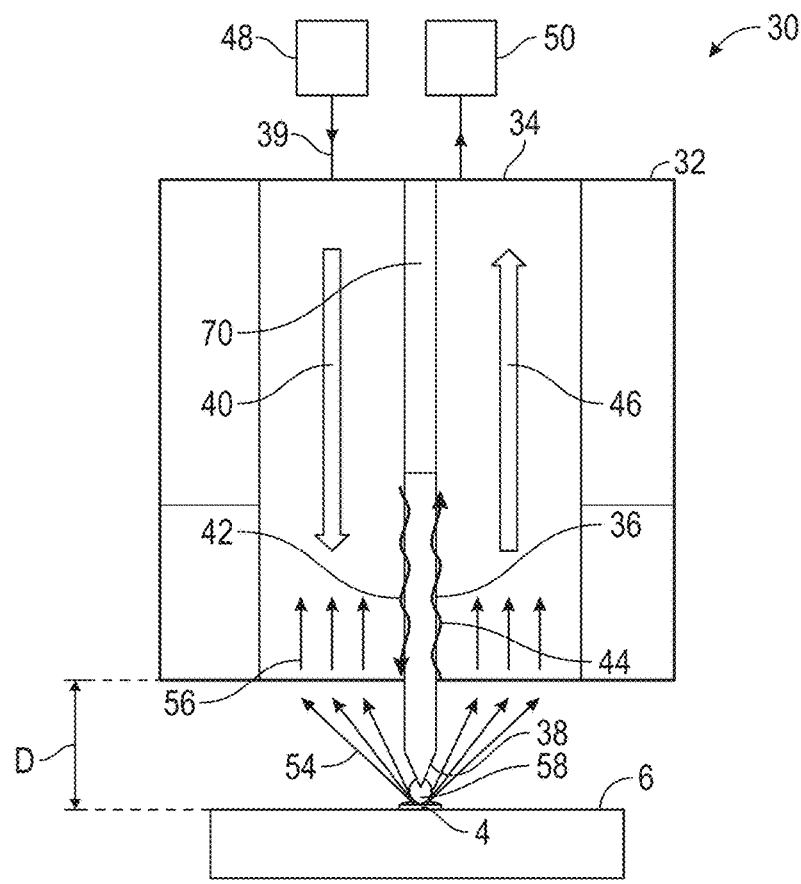
FIG. 2B is a schematic diagram of the TERS system with an example of a plasmonic tip of conducting material, such as a metal tip, in a nano optical fiber that shows the EMR excitation signal into the tip and the resulting signal back through the tip.
Figure 3:
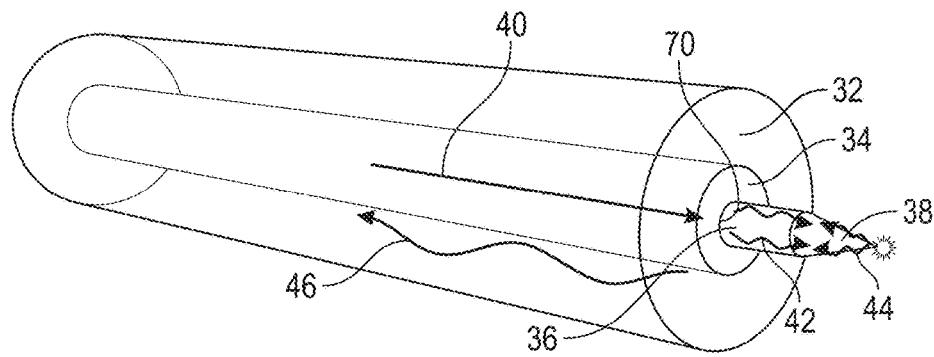
FIG. 3 is a schematic diagram of the plasmonic metal tip illustrated in FIG. 2B.
Figure 4:
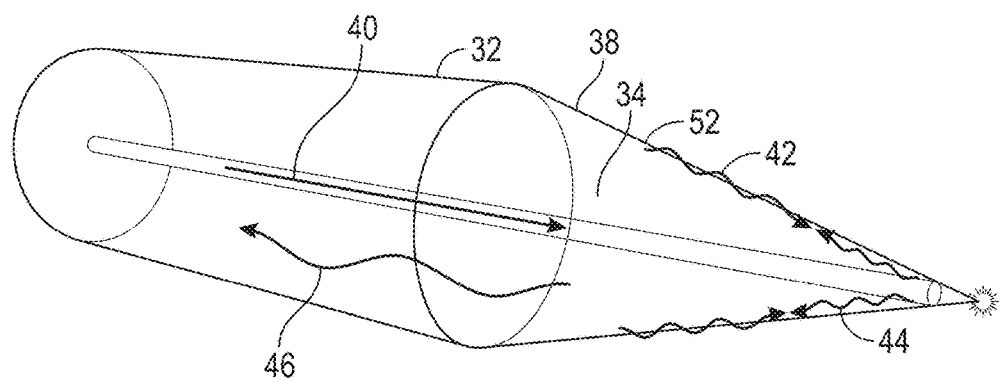
FIG. 4 is a schematic diagram of another example of a tip having conducting plasmonic material coated on the tip.
Figure 5:
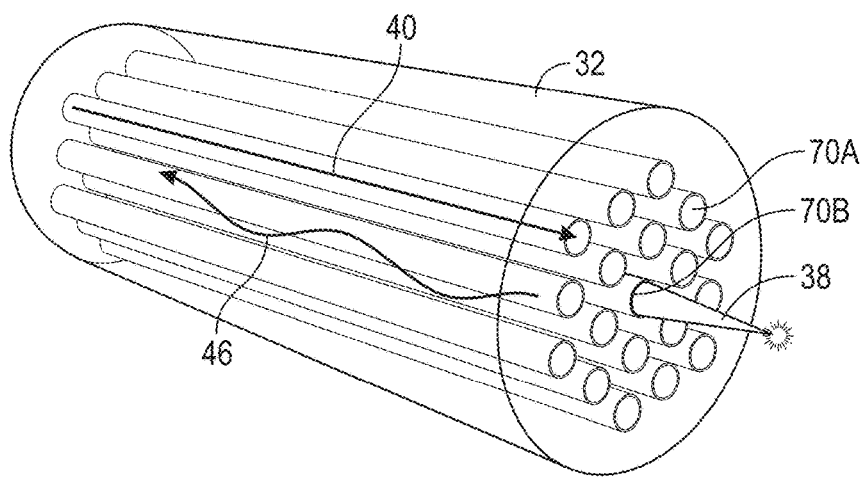
FIG. 5 is a schematic diagram of another example of a plasmonic tip, such as a metal tip, in a photonic crystal fiber.

FIG. 3 is a schematic diagram of the plasmonic metal tip illustrated in FIG. 2B. FIG. 4 is a schematic diagram of another example of a tip having conducting plasmonic material coated on the tip. FIG. 5 is a schematic diagram of another example of a plasmonic tip, such as a metal tip, in a photonic crystal fiber. The disclosure provides at least three embodiments (including combinations thereof) that three different optical fiber-tip geometries to establish an efficient coupling of plasmonic mode for the fiber-based TERS at various wavelength regions: (I) a metal-tip 38 from a nanowire 36 coupled into a nanobore opening 70 of an optical fiber 32 with a core 34 illustrated in FIG. 3; (II) a plasmonic coating 52 on a fiber tip, such as metal-, conducting oxide-, and/or metal nitride-coated single mode fiber, illustrated in FIG. 4; and (III) a nanowire 36 coupled with a photonic crystal fiber (PCF) 32 with a plasmonic tip 38 illustrated in FIG. 5.

The plasmonic nanostructured optical fibers, which merge the fields of plasmonics and fiber optics, enable the fiber TERS imaging applications. The two-step optical coupling process effectively couples light guided in the fiber to a spatially highly localized optical mode at the tip apex, and collects the Raman signal via the reverse coupling process. The configuration improves the detection sensitivity by high coupling efficiency and can practically suppress the far-field background signal. The fiber-tip assembly can be easily integrated with existing SPM designs. The optical alignment-free design offers adaption for applications in various gaseous and liquid environments. The capability of the fiber TERS is further extended to electrically tunable TERS, for example, by the integration of metal/insulator/TCOs nanofilms onto the fiber probe.

In one aspect, the system uses the same fiber-tip assembly for the delivery of the light to the nanoscale excitation point and the collection of the Raman signal from the nanoscale emission. The light coupling is a two-step process. The first step is the mode matching coupling between an optical fiber core mode and a plasmonic waveguide (such as with a plasmonic metal thin film, TCO thin film, metal nitride thin film, and/or plasmonic metal nanowire) mode that are integrated as a fiber-tip assembly. The second step is adiabatic nano-focusing of the excited surface plasmon polaritons (SPP) to the tip of the waveguide. This two-step process enables both the efficient waveguide mode coupling and the efficient transduction of propagating SPP into nanoscale excitation. This design significantly improves the collection efficiency via a different collection process than the conventional TERS system. The collection of the Raman signal utilizes the reverse coupling process. A large portion of the Raman signal, which is normally dissipated through the SPP at the conductive tip, couples back to the fiber waveguide mode, and is collected by the fiber.

Figure 6:
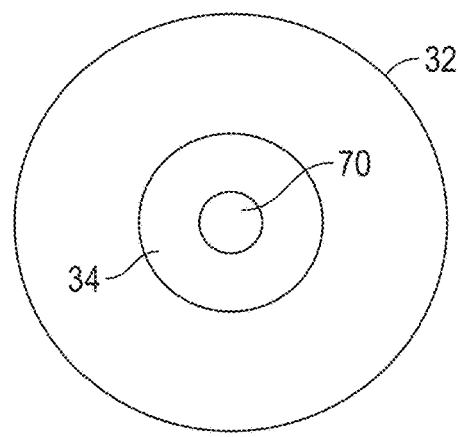
FIG. 6 is a schematic cross sectional diagram of a nanobore optical fiber with an opening in the center.
Figure 7:
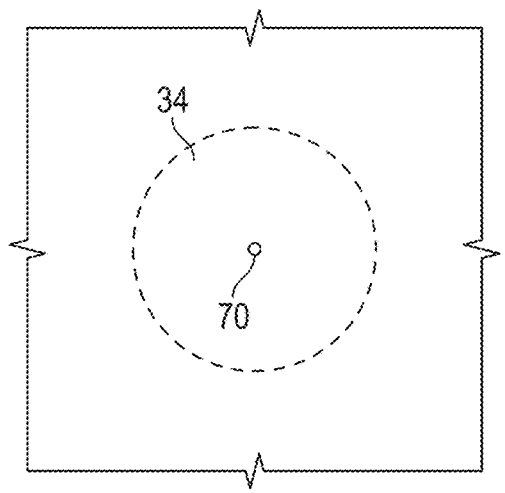
FIG. 7 is a schematic scanning electron microscope image of the nanobore optical fiber illustrated in FIG. 6.
Figure 8:
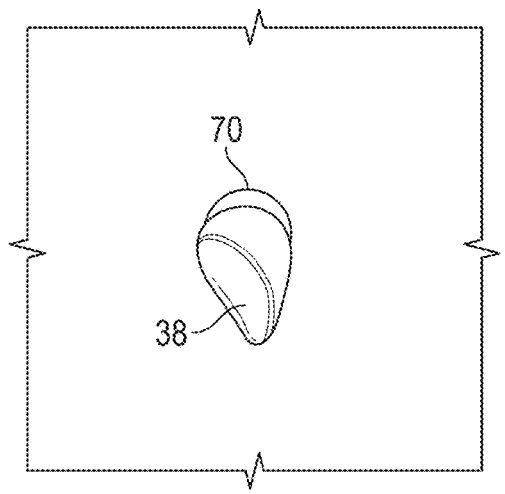
FIG. 8 is a schematic scanning electron microscope image of the nanobore optical fiber illustrated in FIG. 7 that contains a gold field-conducting tip in the opening.

FIG. 2A is a schematic diagram of an illustrative embodiment of an improved TERS system according to the invention. FIG. 2B is a schematic diagram of the TERS system with an example of a plasmonic tip of conducting material, such as a metal tip, in a nano optical fiber that shows the EMR excitation signal into the tip and the resulting signal back through the tip. FIG. 3 is a schematic diagram of the plasmonic metal tip illustrated in FIG. 2B. FIG. 6 is a schematic cross sectional diagram of a nanobore optical fiber with an opening in the center. FIG. 7 is a schematic scanning electron microscope image of the nanobore optical fiber illustrated in FIG. 6. FIG. 8 is a schematic scanning electron microscope image of the nanobore optical fiber illustrated in FIG. 7 that contains a gold field-conducting tip in the opening.

The improved TERS system 30 includes an optical fiber 32 forming a cladding around an internal fiber core 34. The size of the optical fiber can vary and can be between 200-500 μm, for example and without limitation. The fiber core 34 can be doped, including but not limited to a silica, including a GeO2 doped silica. The optical fiber generally includes an nano-sized opening 70 formed as a cavity, bore, or hollow along the length of the optical fiber (generally, a "nanobore" or "opening" herein). The opening 70 can be coupled with a conductive nano-sized guidewire 36 (also referenced herein as "nanowire") tapered to a tip. The material is generally a metal, and advantageously gold or silver. The guidewire 36 can vary in size and generally be about 200-500 nm in diameter, for example and without limitation. The guidewire 36 is formed with a tip 38 at the end of the guidewire facing the sample 4, generally supported by the support 6. The tip 38 is comparatively small to the guidewire diameter and can be 2-20 nm at the end of the tip, for example and without limitation. The material of the tip (and generally the guidewire) 38 is advantageously gold, although silver and copper and potentially other conductive metals can be used. An illustrative distance D from the end of the optical fiber 32 to the support 6 can be between about 500-3000 nm. A receiver/analyzer 50 (which may be in multiple components) is coupled to the optical fiber 32 and to receive and analyze the resulting EMR signal coupled back from the sample 4.

A controller 48 can be coupled to various components of the system 30 for powering an EMR source, for moving the tip such as a scan tube, or other functions to enable the system to function in at least the manner described herein. The controller can include or be coupled with one or more subcontrollers, switches, sensors, and other components beneficial for its functions.

In general, the controller 48 can provide EMR at one or more frequencies to the optical fiber 32 as an excitation EMR, the frequency being at a plasmonic resonance with the plasmonic tip to transmit the excitation EMR through the optical fiber to the tip. The EMR is transmitted from the tip into a sample that changes the vibrational status of the sample that in turn creates a signal EMR that is different from the excitation EMR. The signal EMR is transmitted back to the tip and through the optical fiber to the receiver 50 for analysis.

In operation, the controller/power supply 48 can provide an excitation EMR 40, such as a laser beam, through the fiber 32 and its core 34 that is coupled to the guidewire 36 with the tip 38. The frequency of the excitation EMR 40 is at a resonant frequency that causes plasmonic vibration and transmittance of the excitation EMR through the guidewire to the tip 38. The excitation EMR at the tip is transferred through a space 58 to interact with the sample 4. The interaction results in some EMR elastic scattering at essentially the same frequency that can be filtered out. The interaction also results in some EMR inelastic scattering at a slightly different frequency than the excitation EMR 40 frequency and is collected to form a resulting signal EMR for characterizing the sample material. The signal EMR is generally transmitted back along the tip 38, guidewire 36, and fiber 34 to a receiver/analyzer 50, such as a spectrometer, for processing. The excitation EMR and signal EMR can be generally transmitted both directions along the guidewire and fiber at essentially the same time due to the slightly different resulting frequency of the inelastic scattering.

More specifically, the system 30 such as with the controller 48 creates an EMR at a predetermined plasmonic resonance frequency to form an excitation EMR 39. The excitation EMR is at least partially converted to a wave guide excitation EMR 40 and the wave guide EMR is guided along the optical fiber 32 to the nanowire 36 (if present in the particular embodiment) and in general toward the tip 38. At the nanowire, the wave guide excitation EMR 40 is at least partially converted to a plasmonic excitation EMR 42. The plasmonic excitation EMR 42 propagates along the nanowire 36 and the tip 38. At the tip (generally, the apex of the tip), the plasmonic excitation EMR is transferred across the space 58 to the sample 4. The transferred excitation EMR changes a molecular vibrational status of the sample and creates a reflected signal EMR from the sample at a different frequency than the transferred excitation EMR from the tip. The reflected signal EMR is at least partially transferred back to be received by at least the tip 38 and creates a plasmonic signal EMR 44. The plasmonic signal EMR is propagated along the tip 38 and the nanowire 35 to the optical fiber 32. The plasmonic signal EMR is converted to a wave guide signal EMR 46 and guided along the optical fiber 32 to the receiver 50. The receiver can analyze the signal EMR from the optical fiber to determine at least a characteristic of the sample.

In some embodiments, such as other embodiments described herein, the nanowire may not be used. Instead, a plasmonic coating can be placed on a fiber tip to perform a similar function. In such embodiments, the above description can be adjusted for the plasmonic coating instead of a nanowire.

Figure 9:
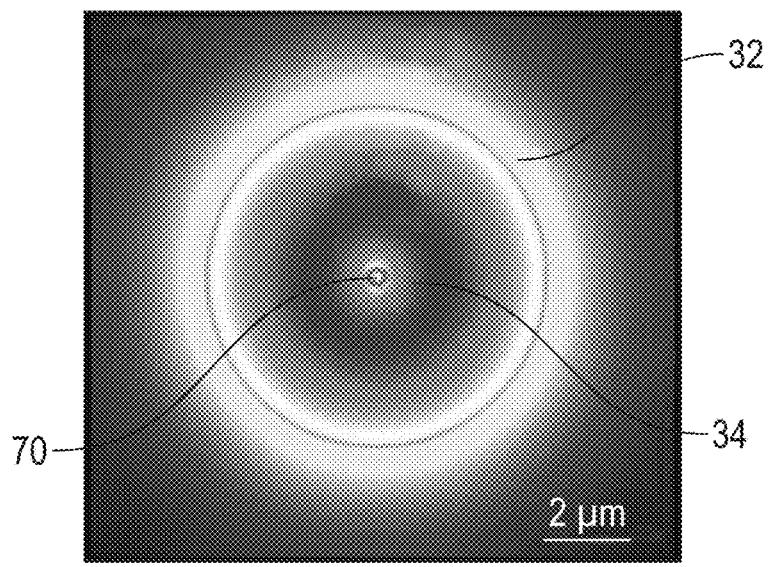
FIG. 9 is a schematic cross sectional view of an optical simulation of the core mode of the optical fiber.
Figure 10:
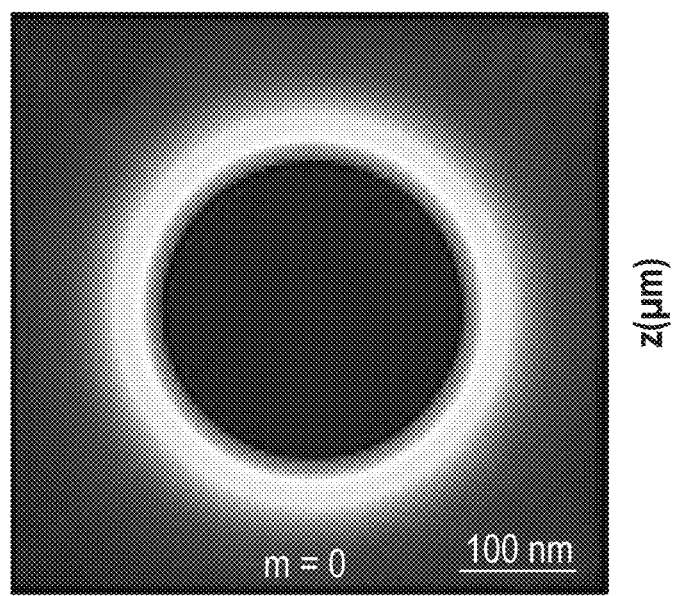
FIG. 10 is a schematic cross sectional view of a field profile of a fundamental plasmonic mode to be coupled.
Figure 11:
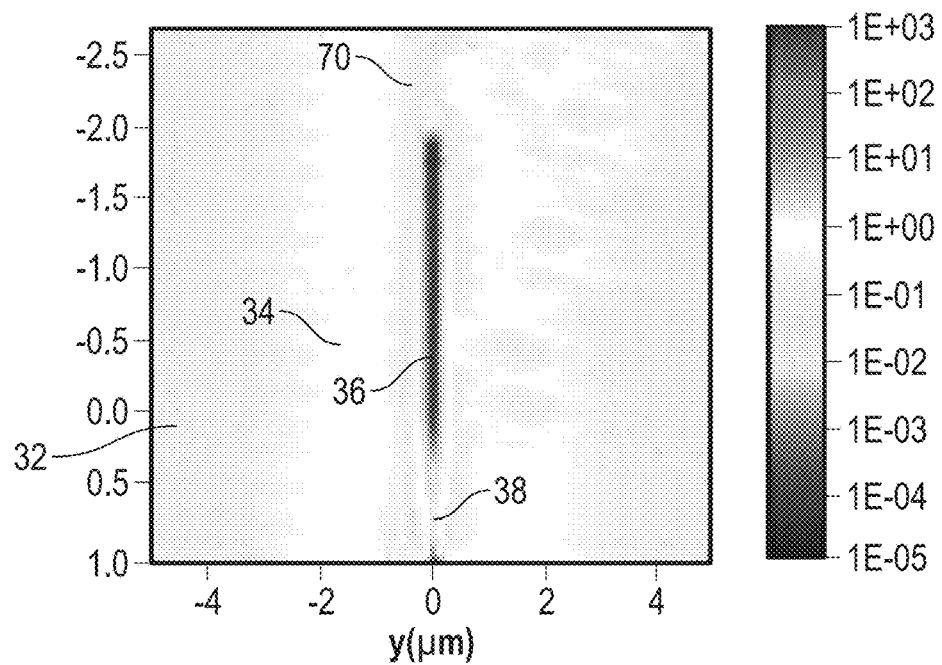
FIG. 11 is a schematic longitudinal view of a simulated field profile by excitation from a dielectric core mode of the nano bore fiber having with a conducting metal in the opening.
Figure 12:
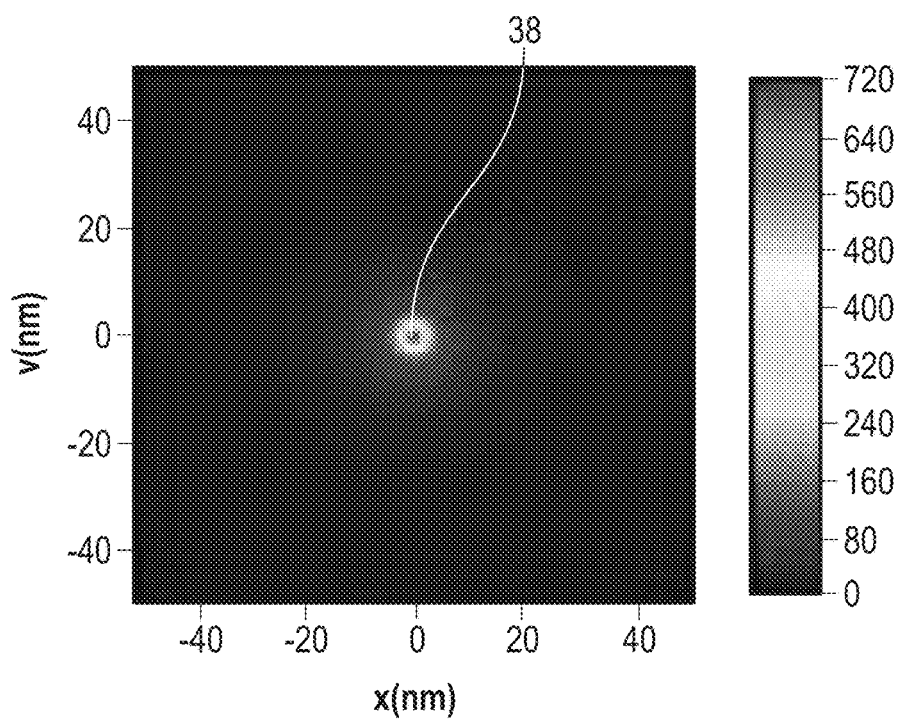
FIG. 12 is a schematic end view of a simulation field focused at the tip showing a Raman resolution of approximately two nm with the present invention.

In conjunction with the system description in FIGS. 2-8, the following figures illustrate results from simulations of the system. FIG. 9 is a schematic cross sectional view of an optical simulation of the core mode of the optical fiber. FIG. 10 is a schematic cross sectional view of a field profile of a fundamental plasmonic mode to be coupled. FIG. 11 is a schematic longitudinal view of a simulated field profile by excitation from a dielectric core mode of the nano bore fiber having a conducting metal in the opening. FIG. 12 is a schematic end view of a simulation field focused at the tip showing a Raman resolution of approximately two nm with the present invention.

The benefit of this nanobore fiber is its high optical confinement. The nanobore optical fiber transmits a large portion (approximately 90%) of the optical energy confined in the nanoscale central hollow channel in the guided core. The comparable sizes of the propagating waveguide (~4 μm diameter) and the nanowire (200 nm-1 μm diameter) provides an advantageous mode match. Conductive nanowires can support guided plasmonic modes, some of which can exhibit unusually low losses. For instance, the propagation loss of the fundamental plasmonic mode shown in FIG. 10 is ~1 dB/mm for gold nanowire diameter of 500 nm. Therefore, the propagation loss can be negligible for nanowire with length of ~100 μm. Because the fundamental plasmonic mode does not exhibit the modal cut off, the highly confined mode could be guided to the end of the tip when the nanowire is tapered, as shown in FIGS. 8, 11, and 12.

The plasmonic action causes free electrons on the surface of the guidewire 36 and tip 38 to shift around at about the same frequency of the EMR in a resonant condition that allows a plasmonic excitation EMR 42 to be propagated along the surface of the guidewire 36. The plasmonic interaction of the excitation EMR with the guidewire results in a plasmonic excitation EMR being propagated along the surface of the guidewire and concentrated at the tip. The result in FIG. 11 shows a strong coupling to the plasmonic mode on the wire and forming a "hot spot" at the end of the tip as further shown in FIG. 12. The excitation EMR then interacts with the sample 4 across the space 58 between the tip and the sample by changing the molecular vibrational status of the sample. The change results in the output of a signal EMR from the sample at a slightly different frequency than the excitation EMR, yet still in the plasmonic region. The signal EMR is transferred across the space 58 back to the tip 38 to create the plasmonic signal EMR 44, and propagates along the surface of the guidewire 36. The plasmonic signal EMR 44 is converted a wave guide signal EMR 46 in the optical fiber 32 and the core 34 at the slightly different frequency than the wave guide excitation EMR 40. Thus, the wave guide excitation EMR 40 and the resulting wave guide signal EMR 46 and their plasmonic EMR components 42 and 44 can be carried on the same optical fiber and guidewire. The wave guide signal EMR 46 is received by the receiver/analyzer 50 for processing.

Further, scattered EMR 54 occurring at different angles caused by molecules on the sample 4 (or the support 6) can be transmitted to the fiber 32 and the core 34 to create a different signal EMR 56 than the signal EMR 44 propagated along tip 38 and the guidewire 36. To receive a large percentage of the scattered EMR 54, it is advantageous to locate the end of the fiber in proximity to the sample. The wavelength of scattered EMR (as Raman signals) is generally only slightly shifted from the wavelength of the excitation EMR and is in the plasmonic range.

Thus, the system 2 in conjunction with the guidewire 36 and the fiber 32 can collect signal EMR through the core 34 from the guidewire plasmonic interaction, collect signal EMR through the core from the scattered EMR, or collect both types of signal EMR.

To integrate the conductive nanowire into the opening, such as the hollow nanobore of the optical fiber, a metal filling technique can be used that applies high-temperature pressure and pressure-assisted melt filling to the opening. Length-to-diameter (aspect) ratios of 100,000 have been achieved, and the nanowires are inherently free of impurities, as no chemical precursors are used. The technique used to fabricate the nano-sized probes as a guidewire with a tip in this embodiment does not require any sophisticated nanostructuring or deposition equipment. For example, a gold filling in the fiber opening can be cleaved and a gold nanotip will form naturally as shown in FIG. 8 with a pliable conductive materials.

As referenced above regarding FIG. 4, in another embodiment of the optical fiber with a tip to form an fiber tip, the fiber tip can be coated with a plasmonic coating 52. In at least one embodiment, the layer can be a thin conductive layer of metal, such as gold or silver; conducting oxide, and/or metal nitride thin films. The light through the optical fiber illuminates the fiber tip, and an evanescent wave penetrates through the metal film. Plasmons are excited at the outer side of the film. In the coated conical fiber tips, the waveguide fiber mode resonantly excites the SPP on the metal surface. The SPP then is confined or otherwise focused at the apex of the tip. A metal coating, such as with gold or silver, is applicable in the visible region of the electromagnetic spectrum. The metal nitride-coated conical tip extends the application of TERS into the near-infrared region, which is desirable in biological media.

The conducting oxide offers a benefit of a tunable TERS. By applying bias voltage, the resonance of the tip can be tuned to match both the laser excitation and the resonance of the molecule-substrate complex to improve the TERS sensitivity and study the optically resonant states and non-resonant states. In contrast, once a gold-coated conical tip is fabricated, the plasmonic resonance of the tip is determined. The resonance would either match the laser or match the resonance of the molecule but rarely both, which limits TERS measurements to a confined range of molecules.

To fabricate the coated fiber tips, an example of a non-limiting process includes chemical fiber etching to form the tip and thin film deposition from radio frequency sputtering, atomic layer deposition, chemical vapor deposition, or other techniques. For example, the conical fiber tips can be etched in hydrofluoric acid with a small layer of mineral oil on top to help prevent the hydrofluoric acid from evaporating. The tip angle can be controlled by the length of time that the fiber is etched, with a longer etching time resulting in a larger tip angle. A programmed motor-controlled translational stage is used to precisely control the etch time for a desired tip angle. This process produces a reproducible tip angle. After the etching, gold, metal oxides, such as indium tin oxide (ITO), metal nitrides such as titanium nitride, or other plasmonic materials as a thin film can be deposited on the fiber tips. The ITO or other conducting oxides as thin films with different carrier concentrations can be tuned by varying an oxygen flow rate during sputtering or other deposition techniques.

Figure 13:
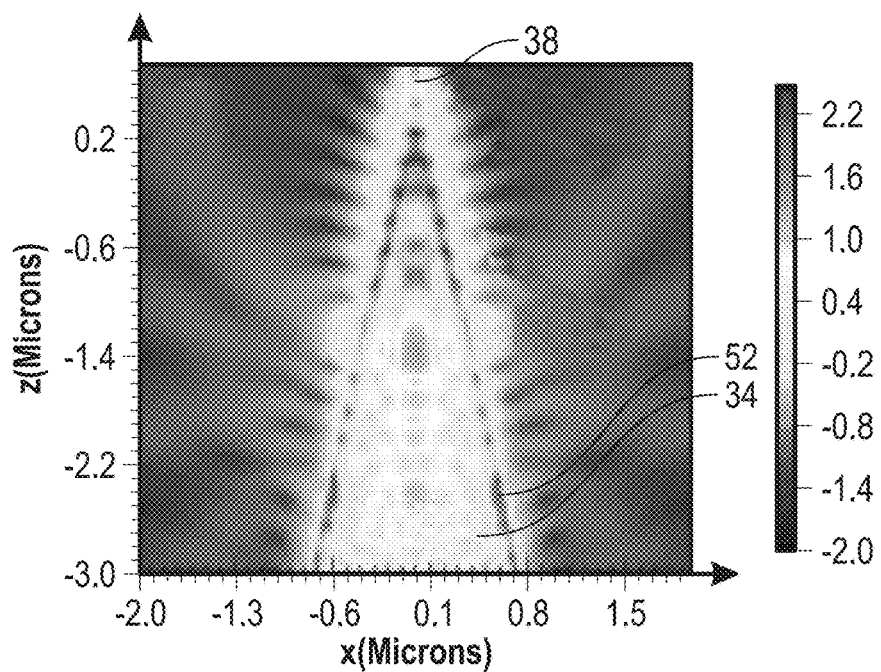
FIG. 13 is a schematic full wave electromagnetic simulation of a tip having a conducting coating.
Figure 14:
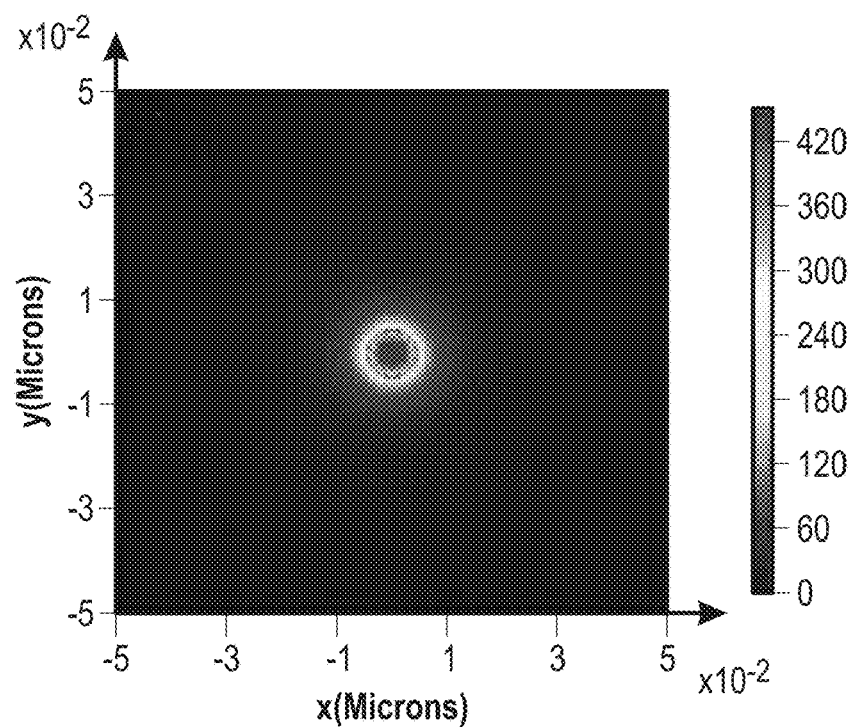
FIG. 14 is a schematic end view of the coded tip of FIG. 13, showing a hotspot at the tip apex.

FIG. 13 is a schematic full wave electromagnetic simulation of a tip having a conducting coating. FIG. 13 shows the coupling of the waveguide mode of the optical fiber core 34 to the surface plasmon polaritons (SPP) mode and the focusing of the light at the apex of the tip 38. FIG. 14 is a schematic end view of the coded tip of FIG. 13, showing a hotspot at the tip apex. Simulations (and optical experimental measurements) have demonstrated efficient coupling between the optical fiber core waveguide mode and the plasmonic mode on a coating 52 of noble metal. When the wave vectors of waveguide mode (TM01) and plasmonic SPP mode (TM0) correspond, energy transfers from the fiber mode to the SPP mode takes place, and as a result, surface plasmons are excited. A simulation shows that the coupling efficiency can be as high as 36%. This amount is comparable with what is analytically calculated. The longitudinal electrical field vector of the TM0 SPP mode increases as it approaches the tip apex because of the shrinking wavelength. Eventually, the SPP excitation is localized at the cone tip in a nanometer scale spatial region, which results in strong emission as shown in FIG. 13. A simulation has shown that due to this superfocusing effect, the electric field at the tip is at least two orders of magnitude higher than the electric field in the waveguide mode, seen in FIG. 14. Light focusing down to a few nanometers can be achieved over a broad spectral range.

The efficiency of the tip can depend on several factors that can be adjusted with experimentation. Factors can include thickness of the film, the fiber core size, and the taper angle.

For the films coated on the tip with conducting oxide and/or metal nitride, the near-infrared region (NIR) can be used to examining samples, particularly biological samples to reduce fluorescence background. To push the plasmonic coupling wavelength to NIR, instead of coating a metal such as gold on the fiber conical tips, a conducting oxide or metallic nitride thin film can be coated. Transparent conducting oxide (TCO) (e.g. indium tin oxide (ITO) and aluminum zinc oxide (AZO)) and transition metal nitrides (TMNs) (e.g. titanium nitride (TiN) and zirconium nitride (ZrN)) can exhibit metallic properties (e.g., negative permittivity) in the visible/NIR frequencies due to their high carrier concentration of materials. While the conducting oxides and metal nitrides exhibit metallic properties, their material loss is significantly lower than noble metals such as gold and silver, and can be alternative plasmonic materials. In addition, their carrier concentration could be varied by fabrication conditions or actively tuned electrically. The materials experimentally appear to exhibit an epsilon-near-zero (ENZ) regime ($-1<\varepsilon r<1$) in the visible/NIR spectrum. This characteristic can lead a strong confinement of light and unique properties such as large optical nonlinearity and enhanced emission.

Figure 15:
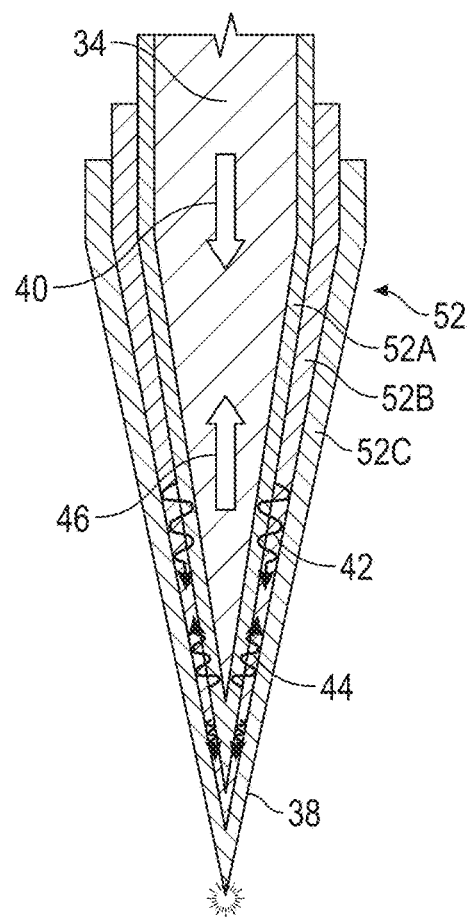
FIG. 15 is a schematic cross sectional view of a tip having a tunable coating, such as a metal oxide semiconductor coating.
Figure 16:
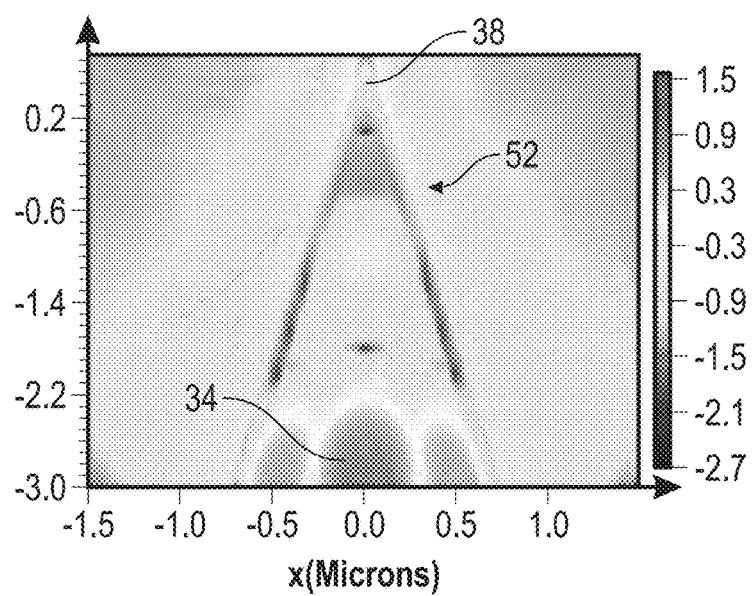
FIG. 16 is a schematic full wave electromagnetic simulation of the tip of FIG. 15.

FIG. 15 is a schematic cross sectional view of a tip having a tunable coating, such as a metal oxide semiconductor coating. FIG. 16 is a schematic full wave electromagnetic simulation of the tip of FIG. 15. FIG. 16 shows the coupling of the waveguide mode of the optical fiber to the plasmonic surface plasmon polaritons (SPP) mode. A further option of a plasmonic coating 52 on a fiber tip is forming a multi-layered combination of a transparent conducting oxide (TCO) 52C, a dielectric layer 52B, and a metal on the tip 52A. The coating 52 can resemble a metal-oxide-semiconductor (MOS) transistor coating on the tip. Applying an electrical bias changes the permittivity of the coating. The field effect-modulated refractive index can change considerably. Using this field-effect dynamic in the MOS-style fiber tip can allow tuning of the coupling wavelength via electrical gating. The ENZ field confinement on the TCO layer can occur with certain applied bias, which can be used to change the ENZ/plasmonic modes coupling and the TERS focusing effects.

Figure 17:
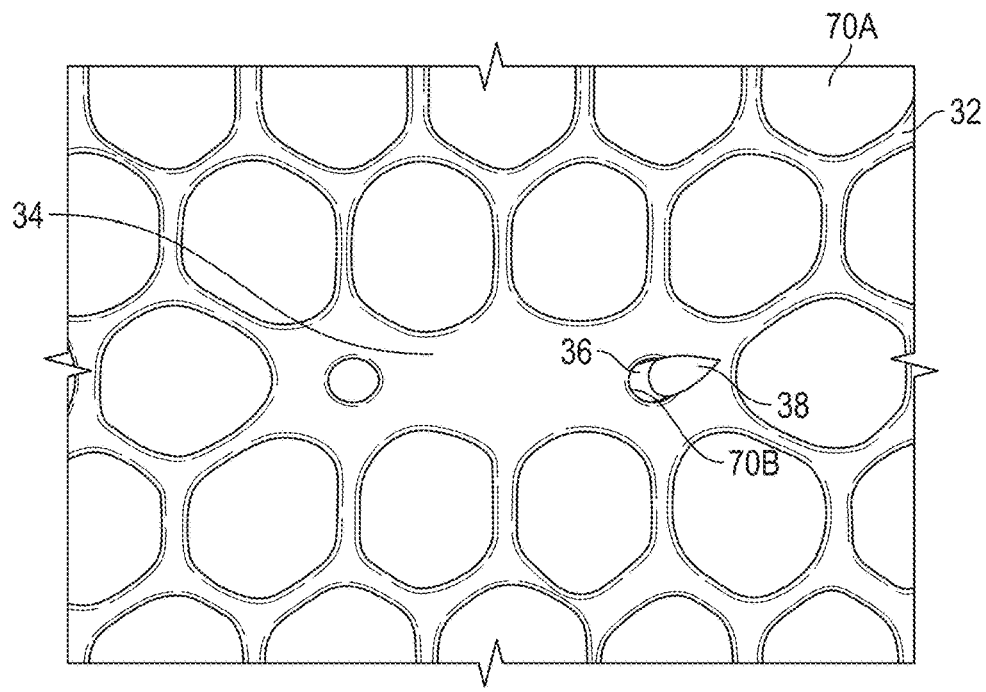
FIG. 17 is a schematic scanning electron microscope image of a holey solid/hollow core photonic crystal fiber with a single metal nano wire in an opening.

FIG. 17 is a schematic scanning electron microscope image of a holey solid/hollow core photonic crystal fiber 32 with a single metal nanowire 36 with a tip 38 in an opening formed by a nanobore opening 70B. As shown in FIGS. 5 and 17, a photonic crystal fiber (PCF) with a tip can be used in another embodiment of the optical fiber with a tip. PCF has an ability to generally confine light in the core 34 of the PCF, such as in the material surrounding the nanobore opening 70B (generally, 70) with the tip 38. (Some light may be present in surrounding openings such as nanobore opening 70A). In general, regular structured fibers such as photonic crystal fibers, have a cross-section (normally, uniform along the fiber length) microstructured from one, two or more materials, most commonly arranged periodically over much of the cross-section, usually as a "cladding" surrounding a core (or several cores) where light is confined. In a solid core PCF, the core has a higher average refractive index than the microstructured cladding, and light can be trapped and guided in the core of the solid core PCF due to modified total internal reflection. Other arrangements include asymmetric cross sections and concentric rings of two or more materials.

The optical properties of PCF can be manipulated by designing the desired glass-air structures, such as shown in FIG. 17 with the unique holey structure and the guiding mechanism of PCFs. The versatility of PCF includes the design of long single mode fibers with single mode propagation for a broad wavelength range, dispersion engineering by modifying the air filling fraction, enhancing the nonlinearity by a small core, creating high birefringence by breaking the symmetry, and hollow-core guiding.

For the application of fiber TERS, PCF can advantageously offer single mode propagation with a broad wavelength range, such as between 400-2000 nm. In addition, an ultra-small guided core diameter (~1 μm) could be designed by arranging the holey cladding structures. High coupling efficiency could be achieved since the modal mismatch between the guided core mode and plasmonic mode could be minimized. Furthermore, the coupling could be realized in a broad wavelength range because of the broadband properties of PCF.

Figure 18:
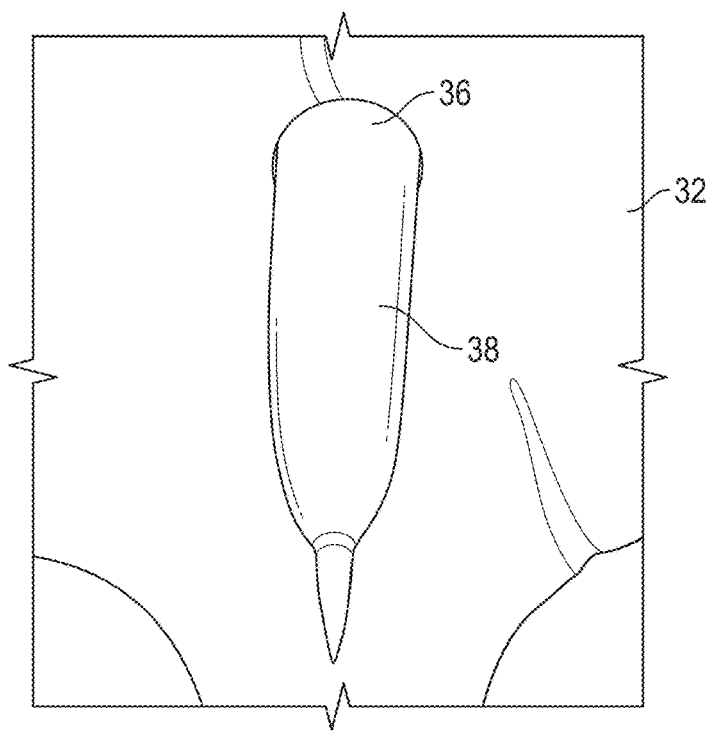
FIG. 18 is a schematic scanning electron microscope image of a metal nano tip in a nanobore of the photonic crystal fiber.

FIG. 18 is a schematic scanning electron microscope image of a metal nano tip in a nano bore of the photonic crystal fiber. In addition, the optical properties of PCFs can be changed by filling the hollow channels with materials such as semiconductors and metals. Using the filling techniques mentioned above for the fiber filled with a nanowire, metallic nanowires can be integrated into optical fibers by using various approaches to pump molten metal, such as gold or silver into the hollow channels of PCF. These metallic PCF include multi/single nanowire filled long single mode fiber, selectively metal-filled polarization-maintaining PCF, single nanowire-integrated nanobore PCF, and single nanowire-filled hollow core PCF.

The small core diameter (~1 μm) and the broadband single mode guiding properties of the nanobore PCF can efficiently excite the plasmonic mode. The small core and broadband single mode guiding properties of the PCF provide an extra degree of freedom to optimize the coupling efficiency between the core mode and the highly confined plasmonic mode. The fabrication of the metal-filled nanobore PCF tip shown as an example in FIG. 18 is similar to the formation of the nanowire with a tip in the fiber opening of FIG. 3 and related figures, described herein.

In addition to the variations in optical fiber and tip materials, the shape of the tip can be adjusted for efficiency. The coupling efficiency and collection efficiency are closely related to the geometry of a probe with the tips, including the diameter and length of a nanowire in the nanobore fiber and PCF fiber that is used to form the tip, the thickness of the thin film on the coated fiber formed as a probe with a tip, and the cone angle of the tip. A sharper tip results in a stronger longitudinal field at the apex and a stronger emission on energy. On the other hand, the cone angle should not be very small; otherwise, the SPP propagation loss can overwhelm the field enhancement, making the SPP localization at the apex insignificant. For example, preliminary simulation shows that for the tips (whether formed from a nanowire, or from the fiber that is coated with plasmonic material), an angle of 28° results in an order of magnitude higher coupling efficiency than an angle of 22°. The coupling efficiency is also closely related to the thickness of the conducting thin film. For tunable TERS, the tunability of the conducting oxide-coated fiber tips is determined by the charge carrier concentration. The charge carrier concentration, fiber specifications, taper angle, and film thicknesses can be changed to modulate the plasmonic coupling wavelength and the coupling efficiency.

The resolution of plasmonic tips is highly sensitive to the polarization state of the input field. Simulations show that the excitation of a radially polarized mode results in a localized hot spot in the near field zone of the tip apex with a peak amplitude higher than the linearly polarized modes. However, the injection of radially polarized beams requires a complicated procedure. Hence, it is desirable to get superfocusing effects similar to those for radial polarization injection by using a linearly polarized mode. Modifications to the originally axially symmetric conical fiber structure have been shown to induce coupling from the linearly polarized modes into the radially polarized modes. Even inherent asymmetries due to the fabrication process can induce this linear to radial mode coupling. Thus, axially asymmetric tips can create radial mode coupling. Examples of axially asymmetric tips are elliptical, tips with facets that can progressively reduce in cross sectional size, and other asymmetric cross sections and surfaces on the tips that break the cross sectional symmetry in a transverse direction to the longitudinal axis of a conical tip. Further, coatings can be applied to not all of the sides of a probe to break the symmetry.

An additional benefit of the TERS system described herein is flexibility in use. For example, the coupling of the excitation EMR signal and the collection EMR signal in the same fiber tip assembly allows portability because the system does not depend on complicated (and fixed) optical alignment. Further, other environments besides air can be used in the analysis, including liquids and electrochemical environments.

In-situ visualizing of electrochemical reactions is a long-standing goal in catalysis, molecular nanotechnology, and biotechnology. Chemical imaging of materials in electrolytes is important for understanding the electrochemistry of electrocatalysts. In this new fiber TERS scheme, the fiber, which guides the light and the imaging nano-tip, are integrated together. This fiber TERS setup can be adopted in various complex realistic environments, e.g. liquid and electrolytes without the modification of the optical alignment. Since the plasmonic mode of the metallic nanowire tip or the conical tip could also be supported with an external medium with higher refractive index than air (for example, water), the plasmonic coupling and field confinement of the TERS fiber tip is believed to not be affected by the external solution as long as it is optically transparent. The plasmon coupling efficiency can increase at the metal-liquid interface in liquid.

Figure 19:
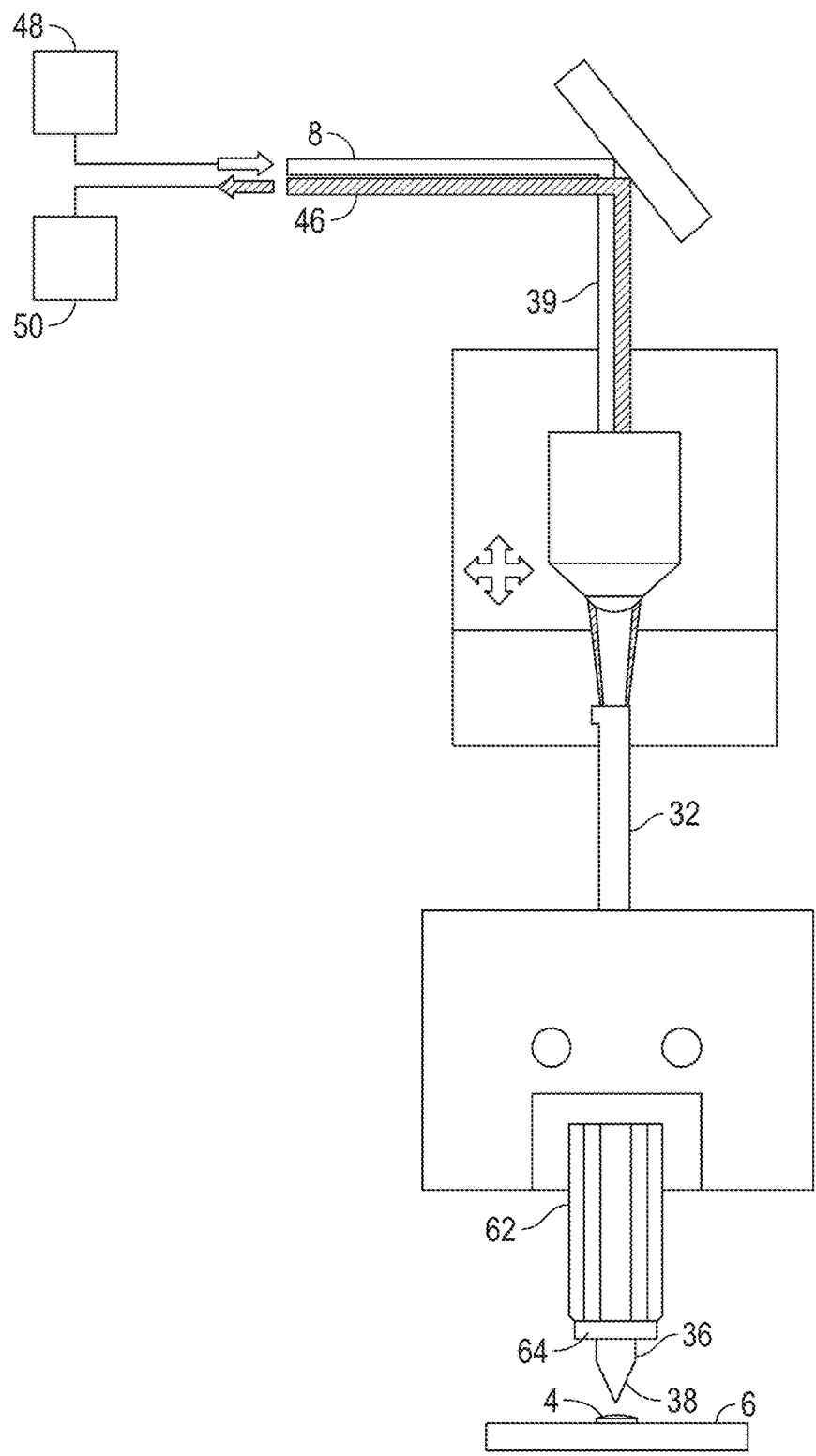
FIG. 19 is a schematic diagram of another embodiment of an improved TERS system according to the invention.
Figure 20:
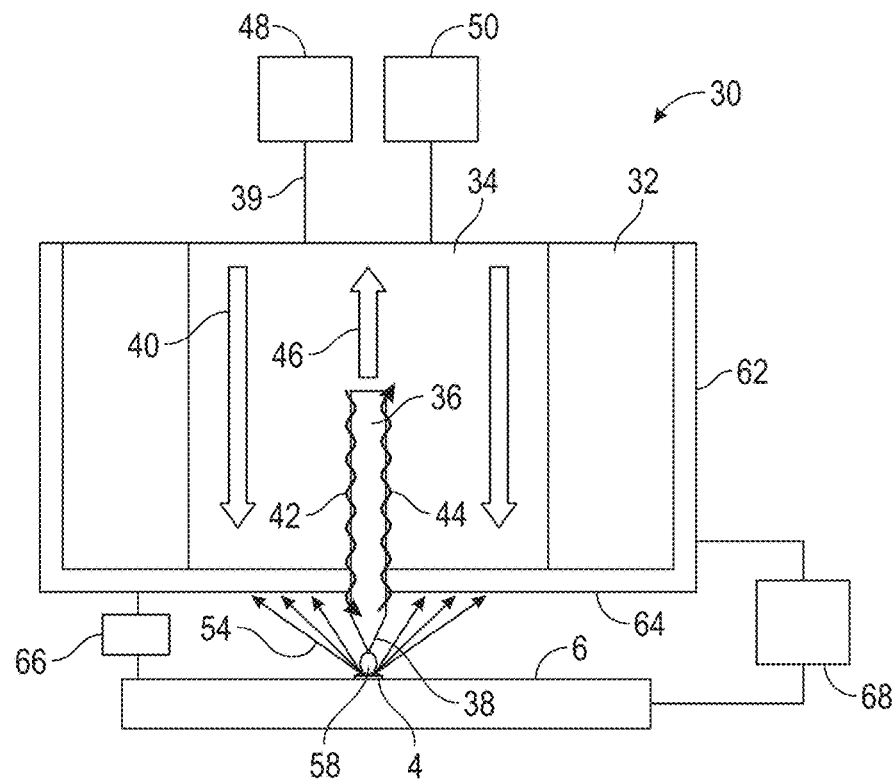
FIG. 20 is a schematic diagram of an enlarged portion of the system of FIG. 19.
Figure 21:
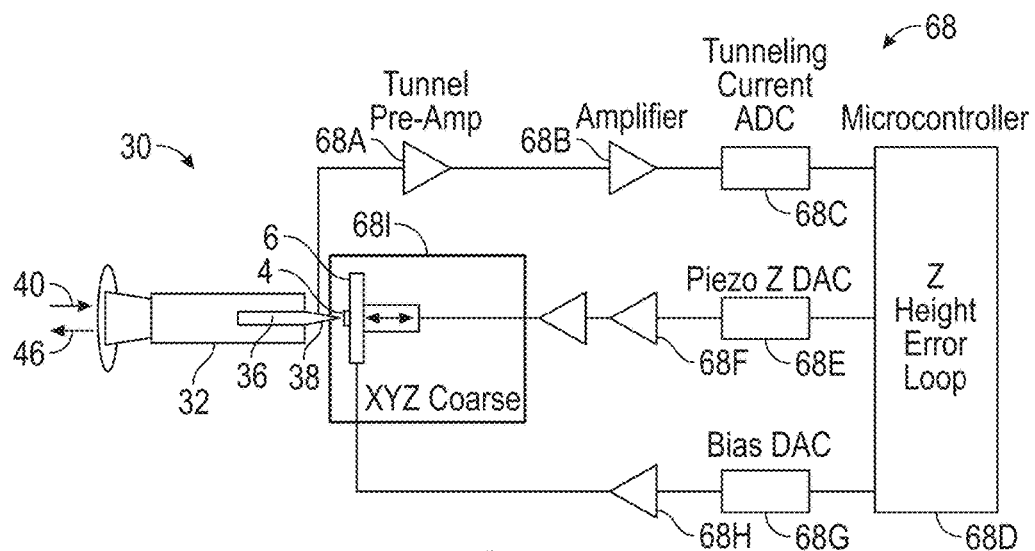
FIG. 21 is a schematic circuit diagram for the illustrative embodiment shown in FIG. 20.

FIG. 19 is a schematic diagram of another embodiment of an improved TERS system according to the invention. FIG. 20 is a schematic diagram of an enlarged portion of the system of FIG. 19 for more detail. FIG. 21 is a schematic circuit diagram for the illustrative embodiment shown in FIG. 20. The system 30 includes features of structure described in the embodiment shown in FIG. 3 and additionally couples such structure to an SPM variation known as a scanning tunneling microscope. A scanning tunneling microscope, as is known in the art, provides for three-dimensional spatial resolution of a sample, but does not provide for collecting a Raman signal to determine the composition of the sample. The present invention offers advantageously the ability to couple the fiber cable 32, nanowire 36 and tip 38 with the plasmonic resonance interaction described above with the scanning tunneling microscope. The combination allows the contemporaneous measurement of a 3-D spatial resolution and composition of the sample.

In general, the system 30 includes an optical fiber 32 and a tip 38. While the above-described embodiment with a doped core 34 and guidewire 36 is illustrated, it is understand that any of the embodiments of optical fibers and tips can be used. The tip 38 is in close proximity to the sample 4 that is supported by a support 6. An electrically conductive layer 62 can be coupled around the fiber 32. Further, an end conductive layer 64 that is conductively coupled with the conductive layer 62 can be coupled with the fiber 32 adjacent an end of the fiber 32. The end conductive layer 64 can also be conductively coupled with the guidewire 36. Further, the end conductive layer 64 (or conductive layer 62) can be conductively coupled to the support 6 with an electronic controller/power supply 66 therebetween.

In operation, the controller/power supply 66 provides a bias voltage to provide tunneling current between the tip 38 and the sample 4 through the support 6. A controller/analyzer 68 provides a measurement of the tip-to-sample distance, which is used to map the topographic and surface features of the sample 4, when the tunneling current is kept constant. The controller/power supply 48 provides an excitation EMR 39, converted to a waveguide excitation EMR 40 through the fiber 32 to form a plasmonic excitation EMR 44 through the guidewire 36 with the tip 38 that is transferred to the sample 4, as described above. The EMR then interacts with the sample 4 by changing a molecular vibrational status of the sample. The resulting signal EMR couples back to the tip 38 and is converted to a plasmonic signal EMR 44 and propagated along the tip 38 and the nanowire 36 (if present) that is converted in the fiber 32 to form the wave guide signal EMR 46. The wave guide signal EMR 46 is collected by the receiver/analyzer 50 for processing.

In some embodiments, the scattered EMR 54 may be restricted from receipt by the fiber 32 due to the intervening layer 64 used for conducting the EMR from the controller/power supply 66 directly to the sample. However, if the layer 64 is conductive and yet at least translucent, then the scattered EMR 54 can be received by the fiber 32 and collected for analysis, as described above.

The invention further provides for pretuning optimal frequency(ies) with a tip. Typically with current TERS systems, several tips (often a dozen or more) are manufactured to attempt to match a tip with an EMR frequency that is suitable for a given application. The testing of each tip to study the results to determine a proper frequency is tedious and further complicated with the requirement of aligning the externally focused EMR to each of the tips for the testing.

With the invention, the EMR is coupled with the tip without requiring an alignment of an EMR at a given frequency to the tip. Thus, a direct reading of responses from the tip at various frequencies can be analysed. For example, a broad band EMR that encompasses a continuum of frequencies can be applied to the tip. The response of the tip to the continuum can be analyzed to select one or more resonant frequencies for a suitable excitation EMR of the tip. The invention allows the system to efficiently pretune an EMR frequency with a tip. The combination of EMR frequency and particular tip can then be applied to testing and analysis of a sample.

Other and further embodiments utilizing one or more aspects of the inventions described above can be devised without departing from the disclosed invention as defined in the claims. For example, other types of scanning probe microscopes can be used in the system including atomic force microscopes, magnetic force microscopes, electrostatic force microscope, and others. Further, although monochromatic light is generally used for such systems, different types of EMR can be used, various guidewires and optical fibers, different doping formulations and concentrations, different materials and coatings for the tips, various shapes of tips, multiple tips, multiple and broadband frequencies, along with other variations can occur in keeping within the scope of the claims, and other variations.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalents of the following claims.

What is claimed is:

1. A spectroscopy system, comprising:
an optical fiber;
a plasmonic tip coupled with the optical fiber configured to be energized into a plasmonic mode;
a controller operatively coupled to the optical fiber and configured to control an electromagnetic radiation (EMR) source to provide one or more frequencies to the optical fiber as an excitation EMR, the frequency being at a plasmonic resonance with the plasmonic tip to transmit the excitation EMR through the optical fiber to the tip;
a receiver operatively coupled to the optical fiber and configured to receive a signal EMR from the tip through the optical fiber, the signal EMR being different from the excitation EMR; and
a power supply configured to apply a bias voltage to the tip and tune the plasmonic resonance of the tip.

2. The system of claim 1, wherein the plasmonic resonance creates a plasmonic excitation EMR along a surface of the tip and the bias voltage is configured to tune the plasmonic resonance of the tip to correspond with the plasmonic excitation EMR.

3. The system of claim 1, wherein the bias voltage changes a permittivity of a tip plasmonic material t tune the plasmonic resonance of the tip.

4. The system of claim 1, wherein the optical fiber is formed with a core and a plurality of longitudinal hollow bores in the optical fiber.

5. The system of claim 1, wherein the optical fiber comprises a photonic crystal fiber.

6. The system of claim 1, wherein the tip is formed from a metal guidewire coupled to the optical fiber.

7. The system of claim 1, wherein the tip is formed from an optical fiber coated with a plasmonic material.

8. The system of claim 7, wherein the plasmonic material comprises metal, conducting oxide, metallic nitride, a metal-oxide-semiconductor multi-layer coating, or a combination thereof.

9. The system of claim 1, wherein the plasmonic tip comprises a plasmonic coating.

10. The system of claim 1, wherein the tip is cross-sectionally transverse asymmetric.

11. The system of claim 1, wherein the controller comprises a power supply.

12. The system of claim 1, wherein the receiver comprises an analyzer.

13. The system of claim 1, wherein the plasmonic resonance creates a plasmonic excitation EMR along a surface of the tip.

14. The system of claim 13, wherein the plasmonic resonance creates a plasmonic signal EMR along a surface of the tip from a reflection of excitation EMR transmitted by the tip to a sample at a different frequency.

15. The system of claim 1, further comprising a conductive layer on an outer surface of the optical fiber and on an end of the optical fiber, the conductive layer being conductively coupled to the tip.

16. The system of claim 15, further comprising a source of a second bias voltage coupled between the conductive layer and a surface supporting a sample to be analyzed with the second bias voltage.

17. The system of claim 15, further comprising a receiver and analyzer coupled to the conductive layer and the surface supporting the sample.

18. A method of analyzing a sample with a spectroscopy system, the spectroscopy, comprising an optical fiber; a tip coupled to the optical fiber; a controller operatively coupled to the optical fiber; and a receiver operatively coupled to the optical fiber, the method comprising:
- creating an electromagnetic radiation (EMR) at a predetermined plasmonic resonance frequency as an excitation EMR;
- converting at least a portion of the excitation EMR to a wave guide excitation EMR;
- guiding the wave guide excitation EMR along the optical fiber toward the tip;
- converting at least a portion of the excitation EMR to a plasmonic excitation EMR;
- propagating the plasmonic excitation EMR along the tip;
- applying a bias voltage to the tip to tune a plasmonic resonance of the tip;
- allowing the plasmonic excitation EMR to transmit a transfer excitation EMR from the tip across a space to a sample;
- changing a molecular vibrational status of the sample with the transfer excitation EMR;
- creating a reflected signal EMR from the sample at a different frequency than the transfer excitation EMR from the tip;
- receiving at least a portion of the reflected signal EMR from the sample across the space to the tip;
- allowing the reflected EMR from the sample to the tip to create a plasmonic signal EMR;
- propagating the plasmonic signal EMR along the tip;
- converting at least a portion of the plasmonic signal EMR to a wave guide signal EMR;
- guiding the wave guide signal EMR along the optical fiber to the receiver; and
- analyzing the signal EMR from the optical fiber to determine a characteristic of the sample.

19. The method of claim 18, wherein a plasmonic material on the tip comprises a conducting oxide or metal nitride, a dielectric layer, and a metal.

20. The method of claim 18, further comprising providing a conductive layer to the optical fiber and conductively coupling the conductive layer with the tip;
- applying a second bias voltage between the tip and the sample through the surface supporting the sample; and
- determining a distance between the tip and the sample based on current as the tip traverses across the sample; and
- determining a topography of the sample based on the distance measurements.

* * * * *